United States Patent
Unno

(10) Patent No.: US 9,597,031 B2
(45) Date of Patent: *Mar. 21, 2017

(54) LYMPHATIC PRESSURE-MEASURING SYSTEM AND METHOD FOR CONTROLLING SAME

(71) Applicants: National University Corporation Hamamatsu University School of Medicine, Shizuoka (JP); Hamamatsu Photonics K.K., Shizuoka (JP)

(72) Inventor: Naoki Unno, Hamamatsu (JP)

(73) Assignee: National University Corporation Hamamatsu University School of Medicine, Shizuoka (JP)

( * ) Notice: Subject to any disclaimer, the term of this patent is extended or adjusted under 35 U.S.C. 154(b) by 4 days.

This patent is subject to a terminal disclaimer.

(21) Appl. No.: 14/659,574

(22) Filed: Mar. 16, 2015

(65) Prior Publication Data

US 2015/0238134 A1 Aug. 27, 2015

Related U.S. Application Data

(63) Continuation of application No. 13/322,988, filed as application No. PCT/JP2010/051706 on Feb. 5, 2010, now Pat. No. 9,042,968.

(30) Foreign Application Priority Data

May 29, 2009 (JP) ................................. 2009-130832

(51) Int. Cl.
*A61B 6/00* (2006.01)
*A61B 5/00* (2006.01)
(Continued)

(52) U.S. Cl.
CPC ............ *A61B 5/418* (2013.01); *A61B 5/0071* (2013.01); *A61B 5/03* (2013.01); *A61B 5/6824* (2013.01);
(Continued)

(58) Field of Classification Search
None
See application file for complete search history.

(56) References Cited

U.S. PATENT DOCUMENTS 3,757,772 A * 9/1973 Goldblat ............ A61B 5/02233
181/131
2005/0124892 A1 6/2005 Weltzel et al.
(Continued)

FOREIGN PATENT DOCUMENTS

CN 1976639 6/2007
JP 2009-539488 11/2009
(Continued)

OTHER PUBLICATIONS

International Preliminary Report on Patentability, dated Dec. 22, 2011, corresponding to International Application No. PCT/JP2010/051706 (filed Feb. 5, 2010), parent of the present application, 4 pp.
(Continued)

*Primary Examiner* — Christopher Cook
(74) *Attorney, Agent, or Firm* — Lathrop & Gage LLP

(57) ABSTRACT

The present invention has an object to measure lymphatic pressure with more safety and ease at lower cost. To achieve this, a lymphatic pressure-measuring system 1 includes: a manchette 11 fitted on a vital observation portion; a measurement unit 13 that measures and outputs pressure of the manchette 11; an infrared camera 21 that detects fluorescence emitted from fluorescent dye previously injected into a lymph vessel in the vital observation portion; and an image processing device 22 that generates and displays an image
(Continued)

showing a position of the fluorescent dye in the lymph vessel based on a detection result of the infrared camera 21. The infrared camera 21 repeats the detection while the pressure of the manchette 11 decreases from first pressure to block a lymph flow in the vital observation portion to second pressure at restart of the lymph flow. The measurement unit 13 repeats the measurement during the period.

7 Claims, 13 Drawing Sheets

(51) Int. Cl.
    *A61B 5/03*     (2006.01)
    *A61B 17/135*     (2006.01)
    *G01B 9/02*     (2006.01)

(52) U.S. Cl.
    CPC .......... *A61B 5/6828* (2013.01); *A61B 17/135* (2013.01); *G01B 9/02* (2013.01); *A61B 2562/043* (2013.01)

(56) References Cited

U.S. PATENT DOCUMENTS

| | | |
|---|---|---|
| 2007/0161926 A1 | 7/2007 | Imamura et al. |
| 2007/0282382 A1 | 12/2007 | Shuros et al. |
| 2008/0183059 A1 | 7/2008 | LaPlante et al. |

FOREIGN PATENT DOCUMENTS

| | | |
|---|---|---|
| KR | 20080083899 | 9/2008 |
| WO | 2007/146489 | 12/2007 |

OTHER PUBLICATIONS

Search Report, dated Mar. 9, 2012, corresponding to International Application No. PCT/JP2010/051706 (filed Feb. 5, 2010), parent of the present application, 1 pp.

Chinese Office Action, dated Jun. 18, 2013, in Chinese Patent Application No. 2010 80023624.5, a related application, 6 pages, Chinese language with English list of cited references.

Japanese Notice of Allowance, dated Jul. 23, 2013, in Japanese Patent Application No. P2011-515916, a related application, 1 page, Japanese language with English list of cited references.

Modi et al. (2007) "Human lymphatic pumping measured in healthy and lymphoedematous arms by lymphatic congestion lymphoscintigraphy," J. Physiol 583(1):271-285.

Unno et al. (2008) "Quantitative Lymph Imaging for Assessment of Lymph Function using Indocyanine Green Fluorescence Lymphography," Eur J Vasc Endovasc Surg 36:230-236.

Unno et al. (2008) "Indocyanine Green Fluorescence Lymphography in Diagnosing Lymphatic Disorders," J Japanese College of Angiology 48(6):531-535, including English Abstract.

\* cited by examiner

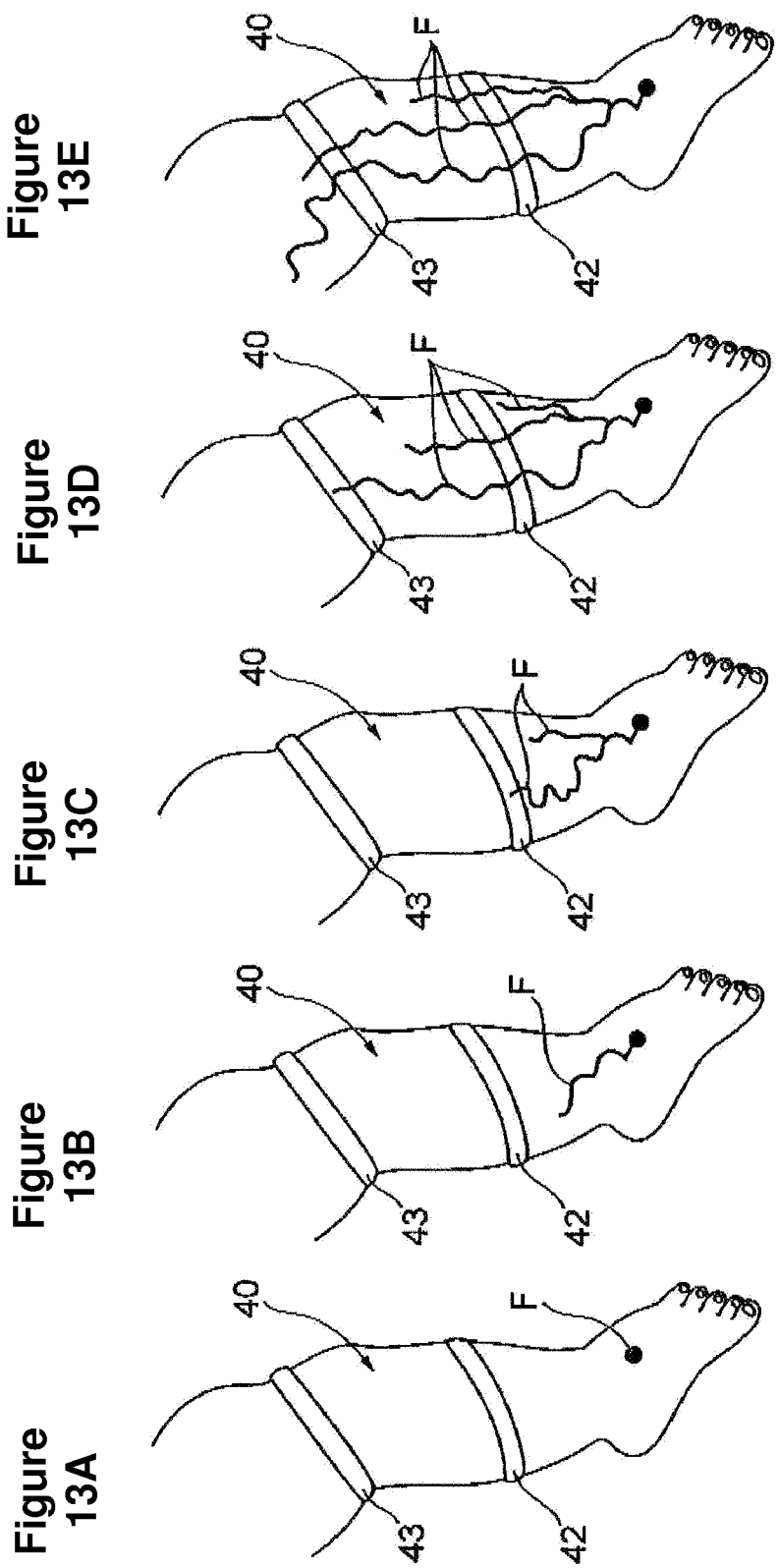

LYMPHATIC PRESSURE-MEASURING SYSTEM AND METHOD FOR CONTROLLING SAME

CROSS-REFERENCE TO RELATED APPLICATIONS

This application is a continuation application which claims the benefit of U.S. application Ser. No. 13/322,988, having a 371(c) date of Jan. 19, 2012, which is a National Stage Application filed under 35 U.S.C. §371 of PCT Application No. PCT/JP2010/051706, filed on Feb. 5, 2010 and published on Dec. 2, 2010 as WO 2010/137358, which claims priority to Japanese Application No. P2009-130832, filed on May 29, 2009, all of which are incorporated by reference in their entireties.

TECHNICAL FIELD

The present invention relates to a lymphatic pressure-measuring system for measuring lymphatic pressure of a human body (particularly, extremities), and a method for controlling same.

BACKGROUND ART

Lymph vessels together with blood vessels run throughout tissues and organs in a body, and are responsible for protection against pathogens, immunity, elimination of waste products, and return of fluid and protein to veins. Lymph flowing through the lymph vessels is pushed out by intrinsic (autonomous) contractility (pumping ability) of the lymph vessels in collecting lymph vessels, and flows through distal portions of extremities to a body trunk, then through a thoracic duct into veins.

However, techniques for measuring pumping ability by intrinsic (autonomous) contractility of lymph vessels have not been established. This is because lymph vessels form an open circuit system unlike blood vessels' closed circuit, direct injection of a contrast dye into lymph vessels is difficult unlike angiography, and thus it is difficult to capture lymph vessels on images. A lymph flow is not a pulsatile flow like an artery, and there is no acoustic detection technique of a lymph flow. Thus, unlike blood pressure measurement, a method for measuring pressure of lymph (lymphatic pressure) flowing through lymph vessels has not been put to practical use. Like blood pressure, lymphatic pressure may be affected by aging or diseases, but this has been hardly clarified because of the technical difficulty mentioned above.

As a method for detecting a lymph flow, a lymphoscintigraphy has been performed as a clinical examination, in which a gamma camera performs scintillation counting of gamma radiation emitted by radio isotopes (RI) injected into skin or subcutaneous tissue and images the gamma radiation. Non-patent Literature 1 mentioned below describes a method for measuring lymphatic pressure of a subject using the lymphoscintigraphy. Specifically, first, a manchette (pressure cuff) is wrapped around an extremity of a subject lying on an examining table of a gamma camera, and the extremity is compressed with certain pressure to stop movement of radio isotopes in lymph vessels. Then, the pressure of the manchette is gradually reduced, and pressure at that time when the isotopes are detected beyond an area around which the manchette is wrapped is measured as lymphatic pressure.

CITATION LIST

Non-Patent Literature

Non-patent Literature 1: Modi S, Stanton A W B, Svenson W E, Peters A M, Mortimer P S, and Levick J R, "Human lymphatic pumping measured in healthy and lymphoedematous arms by lymphatic congestion lymphography," J Physiol, 2007; 583:271-285

SUMMARY OF INVENTION

Technical Problem

However, when the radio isotopes are used as in Non-patent Literature 1 mentioned above, there is a problem that a subject may be exposed to radiation (for example, measurement for pregnant women is impossible), and the isotopes have to be carefully handled and used in a radiation protection facility. In addition, the isotopes are very expensive. From such circumstances, the method described in Non-patent Literature 1 above has not been widely used in clinical practice.

The present invention is achieved to solve the above problems, and has an object to provide a lymphatic pressure-measuring system that can measure lymphatic pressure with more safety and ease at lower cost, and a method for controlling same.

Solution to Problem

The present invention provides a lymphatic pressure-measuring system including: a manchette fitted on a vital observation portion; measurement means that measures and outputs pressure of the manchette; detection means that detects fluorescence emitted from fluorescent dye previously injected into a lymph vessel in the vital observation portion; and display means that generates and displays an image showing a position of the fluorescent dye in the lymph vessel based on a detection result of the detection means, wherein the detection means repeats detection while the pressure of the manchette decreases from first pressure to block a lymph flow in the vital observation portion to second pressure at restart of the lymph flow, and the measurement means repeats measurement while the pressure of the manchette decreases from the first pressure to the second pressure.

The present invention provides a method for controlling a lymphatic pressure-measuring system that includes measurement means, detection means, and display means, including: a measurement step in which the measurement means measures and outputs pressure of a manchette fitted on a vital observation portion; a detection step in which the detection means detects fluorescence emitted from fluorescent dye previously injected into a lymph vessel in the vital observation portion; and a display step in which the display means generates and displays an image showing a position of the fluorescent dye in the lymph vessel based on a detection result in the detection step, wherein in the detection step, detection is repeated while the pressure of the manchette decreases from first pressure to block a lymph flow in the vital observation portion to second pressure at restart of the lymph flow, and in the measurement step, measurement is repeated while the pressure of the manchette decreases from the first pressure to the second pressure.

According to the lymphatic pressure-measuring system and the method for controlling same, the fluorescent dye that reached the lymph vessel is repeatedly detected and an image thereof is displayed in each case and the pressure of the manchette is repeatedly measured and output until the pressure of the manchette decreases from the first pressure to the second pressure. Thus, the pressure (second pressure) of the manchette at the restart of the lymph flow that has been blocked by the pressure of the manchette can be easily recognized as lymphatic pressure. The fluorescent dye does not emit radiation, and can be obtained at low cost. Thus, according to the above technique, lymphatic pressure can be measured with more safety and ease at lower cost without risk of exposure to radiation.

In the lymphatic pressure-measuring system of the present invention, at least a part of the manchette may be formed of a transparent member so that the fluorescence can pass through.

In this case, the detection means can detect the fluorescence having passed through the manchette fitted on the vital observation portion. Thus, as compared to a case where the manchette is formed of only an opaque member, the fluorescent dye in the lymph vessel in the vital observation portion can be detected more quickly, and thus whether the lymph flow has restarted can be determined more quickly.

In the lymphatic pressure-measuring system of the present invention, a scale may be formed in a direction of the lymph flow on the transparent member.

In this case, the scale can be used to measure time for the lymph flow to flow over a predetermined distance to calculate a flow rate of lymph.

The present invention provides a lymphatic pressure-measuring system including: a manchette fitted on a vital observation portion; first detection means that is provided in the manchette and detects fluorescence emitted from fluorescent dye previously injected into a lymph vessel; second detection means that is provided in a position remoter from an injection point of the fluorescent dye than the first detection means in the manchette, and detects fluorescence emitted from the fluorescent dye; pressure adjustment means that increases pressure of the manchette to block a lymph flow in the vital observation portion when the first detection means detects the fluorescence, and then gradually reduces the pressure of the manchette; and measurement means that measures and outputs the pressure of the manchette when the second detection means detects the fluorescence.

According to the lymphatic pressure-measuring system, when the fluorescent dye that reached the lymph vessel is detected at one point (the first detection means) in the manchette, the manchette is pressurized to block the lymph flow in the vital observation portion. Then, the pressure of the manchette is gradually reduced to restart the lymph flow, and when the fluorescent dye on the lymph flow is detected at a different point (the second detection means) in the manchette, the pressure of the manchette at that time is measured. As such, movement of the fluorescent dye is detected to automatically adjust and measure the pressure of the manchette, and thus the pressure of the manchette at the restart of the lymph flow can be easily recognized as lymphatic pressure. The fluorescent dye does not emit radiation, and can be obtained at low cost. Thus, according to the above technique, lymphatic pressure can be measured with more safety and ease at lower cost without risk of exposure to radiation.

In the lymphatic pressure-measuring system of the present invention, each of the first and second detection means may include light application means that applies excitation light to the fluorescent dye, and light receiving means that detects fluorescence emitted from the fluorescent dye having received the excitation light.

In this case, the excitation light is applied to the fluorescent dye, and thus the fluorescent dye that emits fluorescence only when light having a specific wavelength is applied can be used, and fluorescent dye having various wavelength characteristics (having specific excitation light wavelengths) can be used.

In the lymphatic pressure-measuring system of the present invention, the first detection means may be provided at one edge extending in a width direction of the manchette, and the second detection means may be provided at the other edge extending in the width direction of the manchette.

In this case, the detection means may be provided at the opposite edges of the manchette, and thus the manchette can be easily produced.

In the lymphatic pressure-measuring system of the present invention, the first detection means may be provided to linearly extend along one edge, and the second detection means may be provided to linearly extend along the other edge.

In this case, the first and second detection means are linearly provided at the opposite edges of the manchette. Thus, a fluorescence trapping range when the manchette is fitted on the vital observation portion can be broadened to more reliably detect fluorescence.

Advantageous Effects of Invention

According to the lymphatic pressure-measuring system and the method for controlling same, safe fluorescent dye without risk of exposure to radiation can be used to observe whether the lymph flow restarts and measure the pressure of the manchette at the restart as lymphatic pressure. Thus, lymphatic pressure can be measured with more safety and ease at lower cost without risk of exposure to radiation.

BRIEF DESCRIPTION OF DRAWINGS

FIGS. 13A to 13E are schematic diagrams showing fluorescent dye moving through lymph vessels.

DESCRIPTION OF EMBODIMENTS

Figure 1:
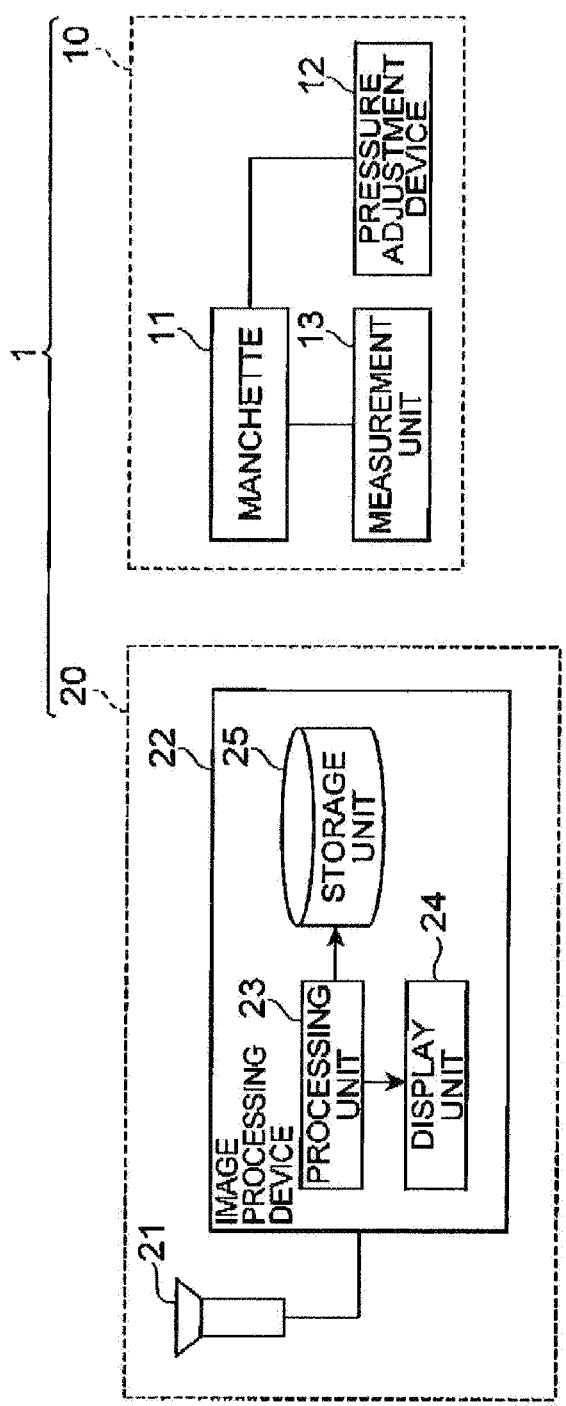
FIG. 1 is a block diagram showing a general configuration of a lymphatic pressure-measuring system according to a first embodiment.

Now, embodiments of the present invention will be described in detail with reference to the accompanying drawings. In descriptions of the drawings, the same or equivalent components are denoted by the same reference numerals, and overlapping descriptions will be omitted.

First Embodiment

First, with reference to FIGS. 1 to 4, a function and a configuration of a lymphatic pressure-measuring system 1 according to a first embodiment will be described.

The lymphatic pressure-measuring system 1 is a group of devices used for measuring lymphatic pressure of human extremities. As shown in FIG. 1, the lymphatic pressure-measuring system 1 includes a lymphatic pressure-measuring device 10 that measures and displays lymphatic pressure, and a lymph flow display device 20 that detects and displays a lymph flow in a lymph vessel.

Figure 2:
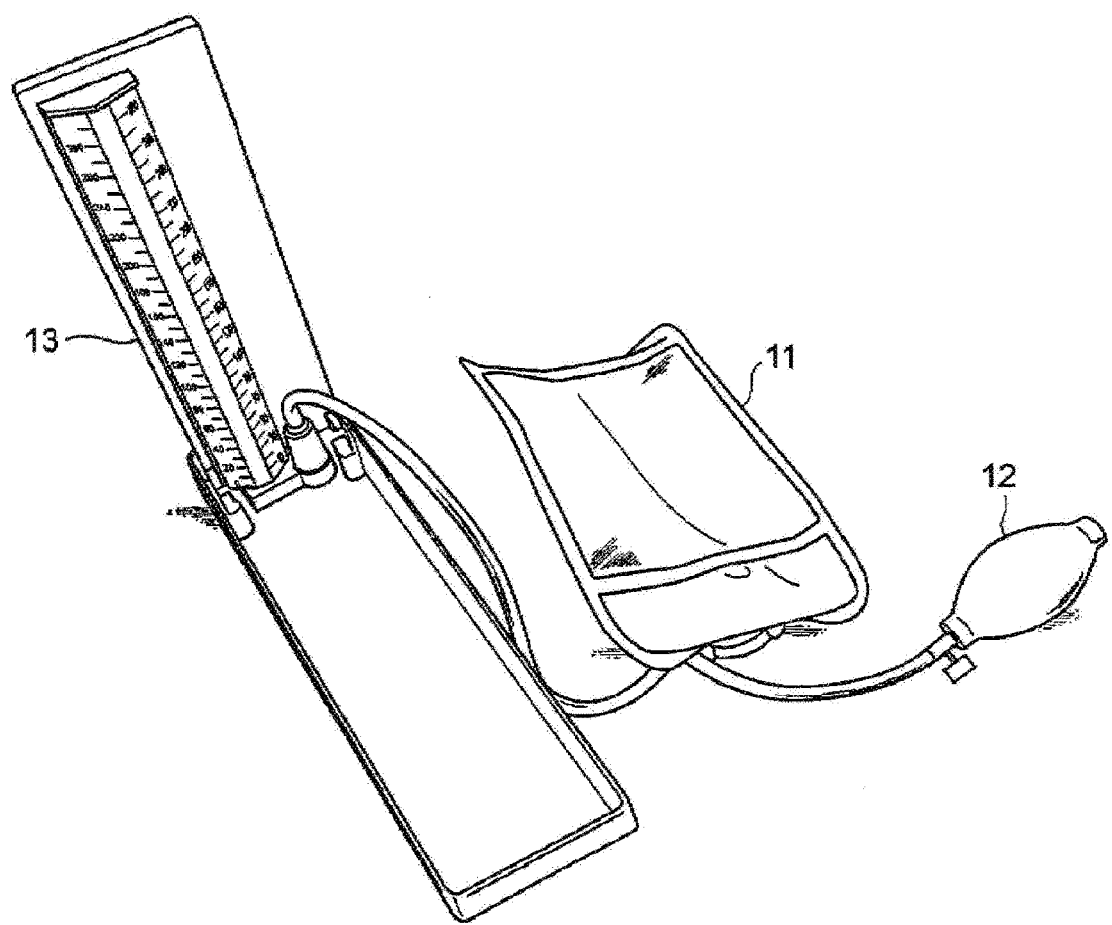
FIG. 2 is a perspective view of a lymphatic pressure-measuring device in FIG. 1.

The lymphatic pressure-measuring device 10 includes, as shown in FIG. 2, a manchette (pressure cuff) 11 that can be fitted on a human extremity, a pressure adjustment device 12 that increases or decreases pressure of the manchette 11, and a measurement unit (measurement means) 13 that measures and displays the pressure of the manchette 11. In an example in FIG. 2, an air supply bulb and a mercury sphygmomanometer conventionally used for measuring blood pressure are used as the pressure adjustment device 12 and the measurement unit 13, respectively.

Figure 3:
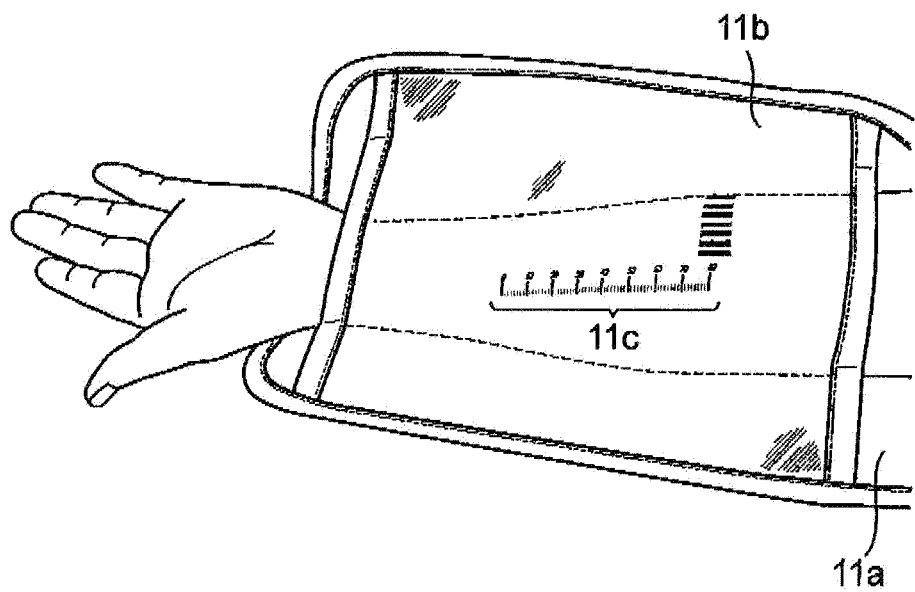
FIG. 3 is a perspective view showing an example of a manchette in FIG. 1.
Figure 4A:
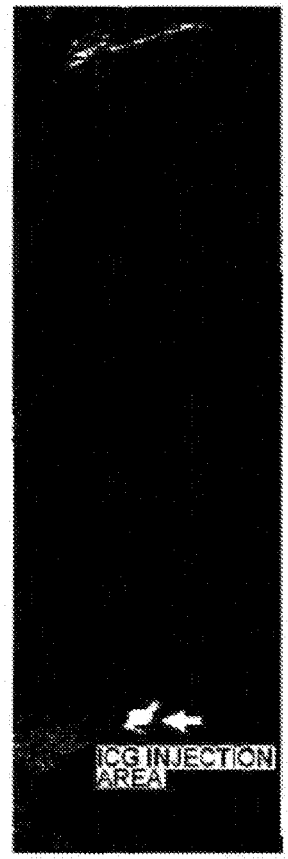
FIGS. 4A to 4D show examples of images displayed by a lymph flow display device in FIG. 1.
Figure 4B:
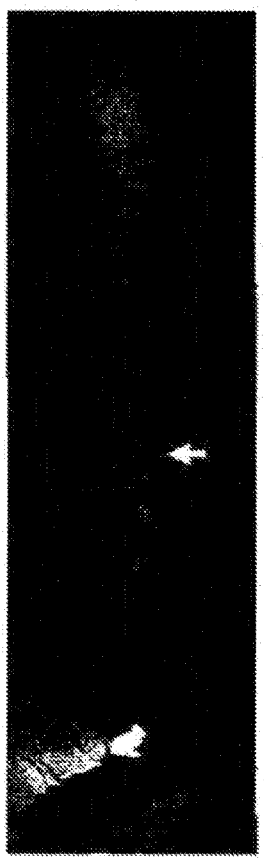
Figure 4C:
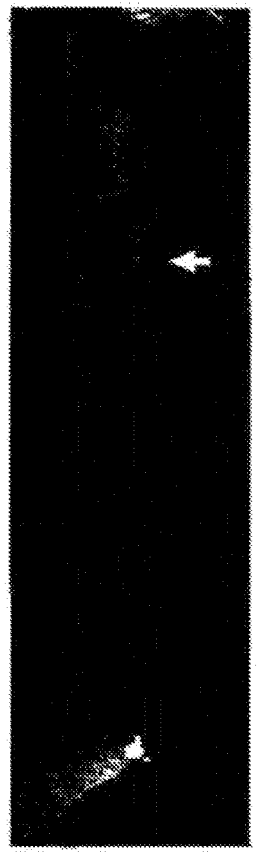
Figure 4D:
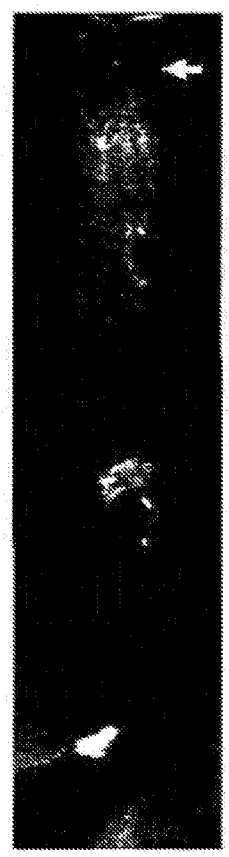

The manchette 11 is fitted around a part of an arm or a leg so as to cover the part. An area on which the manchette is fitted and therearound are referred to as a vital observation portion. The manchette 11 includes an air bag, and the pressure adjustment device 12 supplies air into the air bag to pressurize the covered area. The manchette may have a band-like structure including a hook and loop fastener for securing wrapping, or may have a cylindrical shape through which an arm or a leg can pass as shown in FIG. 3.

In any case, the manchette preferably includes a transparent portion so that skin of the covered area by fitting can be visually recognized. The manchette 11 shown in FIG. 3 includes an air bag 11a (on a lower side of an arm) and a transparent portion 11b (on an upper side of the arm). The air bag 11a and the transparent portion 11b are joined at opposite sides along an insertion direction of the arm or leg. On the transparent portion 11b, a scale 11c showing a distance is printed in the insertion direction. Also when the manchette is of a wrapping type, the transparent portion and the scale can be provided as in the example in FIG. 3.

In order to produce the transparent and pressure-resistant transparent portion 11b, for example, a copolymer of elastomer (rubber) and nylon, polyethylene terephthalate (PET), nylon 12 (polyamide), silicone rubber (silicone), or polyurethane elastomer (polyurethane) may be used. Of course, materials of the transparent portion 11b are not limited thereto.

The configuration of the lymphatic pressure-measuring device 10 is not limited to that shown in FIG. 2, but for example, a digital automated sphygmomanometer conventionally used may be used. In this case, the manchette is preferably formed to be transparent so that the vital observation portion can be visually recognized.

The lymph flow display device 20 includes, as shown in FIG. 1, an infrared camera (detection means) 21 and an image processing device (display means) 22. The infrared camera 21 and the image processing device 22 are connected by a communication cable.

The infrared camera 21 detects fluorescence emitted from fluorescent dye injected into a lymph vessel of a subject in the vital observation portion. The infrared camera 21 is portable and easy to carry. The infrared camera 21 takes an image of a region including the transparent portion 11b of the manchette 11, generates image data including fluorescence having passed through the transparent portion 11b and outputs the image data to the image processing device 22.

The fluorescent dye applied to a subject will be now described. The fluorescent dye is applied by injection to skin or subcutaneous tissue, and then into a lymph vessel. An example of the fluorescent dye is indocyanine green. The indocyanine green is an agent approved in Japan, having very few side effects, and routinely used in general hospitals. The indocyanine green is very inexpensive and easy to handle. As the fluorescent dye, substances such as fluorescent dextran may be used other than the indocyanine green.

The image processing device 22 generates and displays an image showing a position of the fluorescent dye in the lymph vessel based on the image data input from the infrared camera 21. The image processing device 22 includes a processing unit 23, a display unit 24, and a storage unit 25 as functional components. The image processing device 22 may be achieved by installing predetermined software for processing images of the infrared camera 21 in a portable personal computer, or may be designed only for image processing in this embodiment. In any case, the image processing device 22 may be portable like the infrared camera 21.

The processing unit 23 processes the image data input from the infrared camera 21, outputs the image data to the display unit 24, and stores the image data in the storage unit 25. The processing unit 23 can read the image data from the storage unit 25, and output it as a recorded image to the display unit 24. Such functions of the processing unit 23 can be achieved by cooperation between a central processing unit (CPU) and a main storage unit (ROM or RAM) or the like.

The display unit 24 includes a monitor, and displays (visualizes) the image data input from the processing unit 23. Examples of images of the fluorescent dye displayed by the display unit 24 are shown in FIG. 4. In FIG. 4, the fluorescent dye appears white. FIGS. 4A to 4D show that, as indicated by arrows, a fluorescent member injected into the dorsum of a foot moves upward on a lymph flow to groin.

The storage unit 25 is constituted by a storage device such as a hard disk, and stores the image data input from the processing unit 23.

A method for displaying fluorescent dye in a lymph vessel using such a lymph flow display device 20 is described in the reference mentioned below.

REFERENCE

Unno N, Nishiyama M, Suzuki M, Yamamoto N, Inuzuka K, Sagara D, Tanaka H, and Konno H, "Quantitative lymph imaging for assessment of lymph function using indocyanine green fluorescence lymphography," Eur J Vasc Endovasc Surg 2008; 36:230-236

Figure 5:
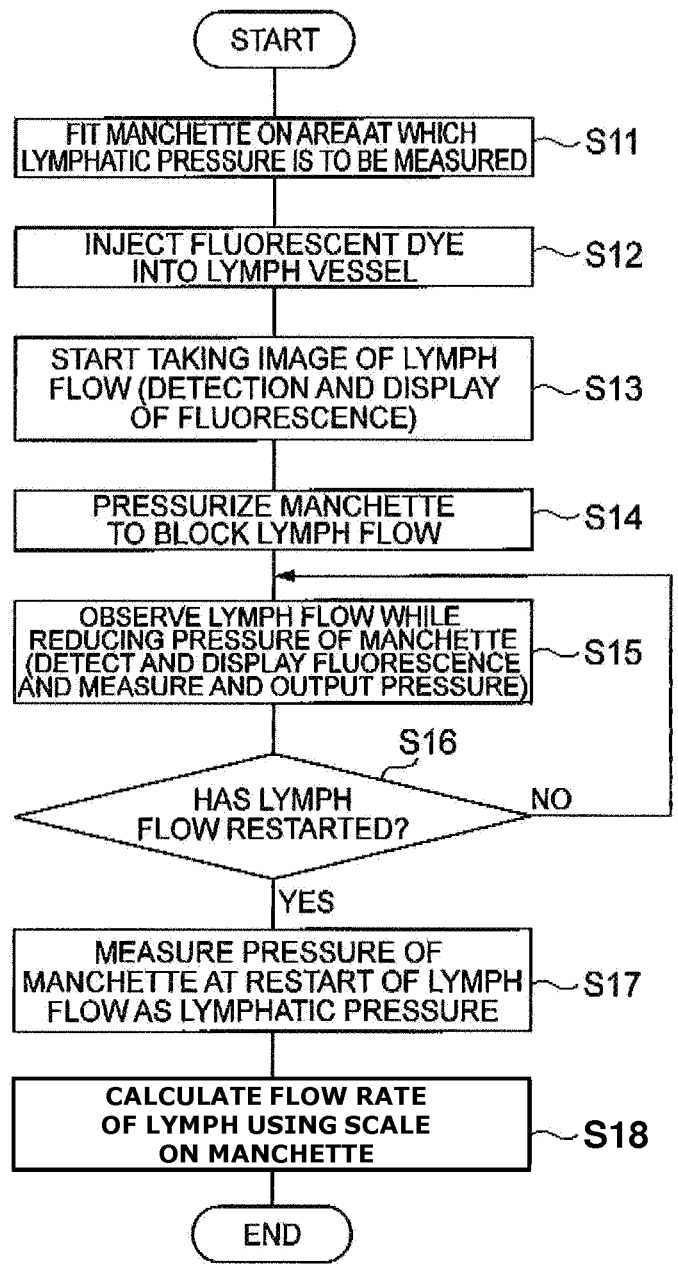
FIG. 5 is a flowchart showing a measurement method using the lymphatic pressure-measuring system in FIG. 1 and a process by the system.

Next, with reference to FIGS. 5 and 6, a procedure for measuring lymphatic pressure of an extremity of a subject using the lymphatic pressure-measuring system 1 will be described, and a method for controlling the lymphatic pressure-measuring system 1 according to this embodiment will be described.

First, the manchette 11 is fitted on an area at which lymphatic pressure is to be measured (vital observation portion) (Step S11). Also, fluorescent dye (for example, indocyanine green) is injected into a lymph vessel of the subject (Step S12). Actually, the fluorescent dye may be injected into skin or subcutaneous tissue of an area (for example, back of a hand or foot) closer to a distal end than the area on which the manchette 11 is fitted, and the fluorescent dye then leads into the lymph vessel. After application of the fluorescent dye, the subject may be in any of standing, lying, and sitting positions, or may do simple exercise.

Figure 6:
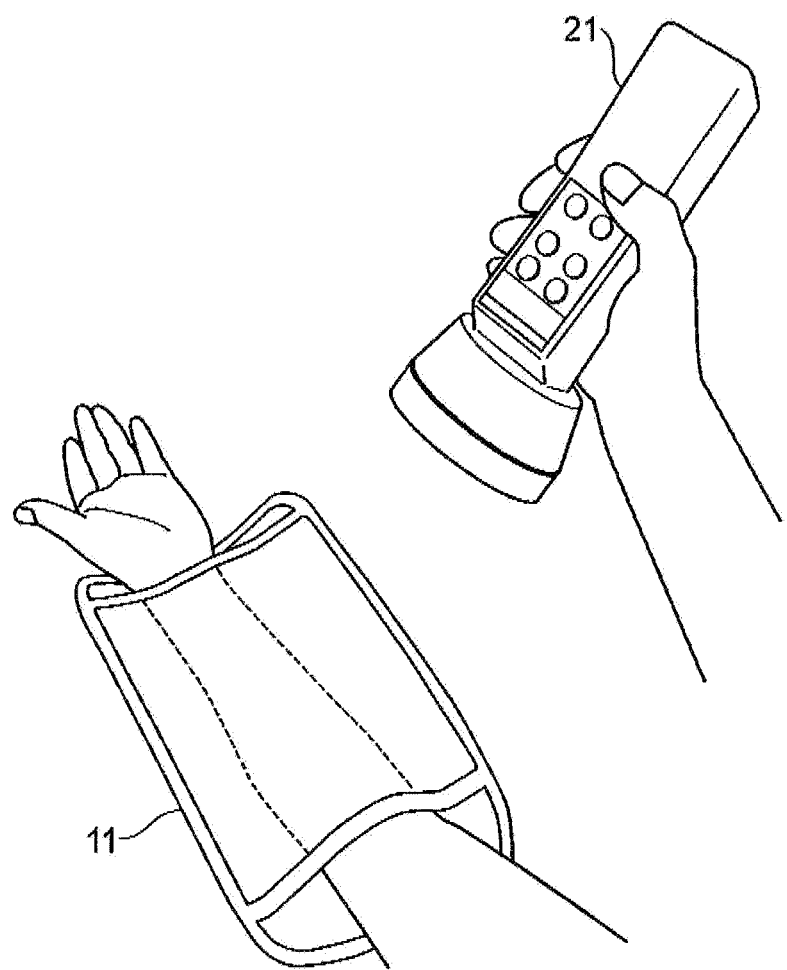
FIG. 6 shows an image taking position of an infrared camera in FIG. 1.

Then, as shown in FIG. 6, an image taking position of the infrared camera 21 is aligned with the region including the transparent portion 11b of the manchette 11, and image taking of a lymph flow is started (Step S13, detection and display step). At this time, the infrared camera 21 captures fluorescence from the fluorescent dye in the lymph vessel, and the display unit 24 displays an image thereof. Returning to FIG. 5, the pressure adjustment device 12 then pressurizes the manchette 11 to block the lymph flow in the vital observation portion (Step S14). Pressure at this time is first pressure.

Then, the pressure of the manchette 11 is reduced in increments of a predetermined amount (for example, in increments of 1 mmHg, 5 mmHg, 10 mmHg, or the like) while image taking is continued, and the lymph flow display device 20 is used to observe whether the lymph flow restarts. At this time, the infrared camera 21 continuously captures the fluorescence from the fluorescent dye, the display unit 24 continuously displays the image thereof, and the measurement unit 13 measures and outputs the pressure of the manchette (Step S15, detection, display and measurement step).

When the lymph flow restarts (Step S16; YES), a measurer visually recognizes the lymph flow and measures pressure (second pressure) of the manchette 11 at that time as lymphatic pressure (Step S17). When the lymph flow does not restart (Step S16; NO), the process in Step S15 is repeated. The restart of the lymph flow means that intrinsic (autonomous) autonomous contractility of the lymph vessel exceeds and the fluorescent dye in the lymph vessel starts to move beyond the pressurized portion of the manchette 11. Also, with a movement distance of the lymph flow measured from the image data including the scale 11c projected in the direction of the lymph flow, and a measurement result of time for the lymph flow to move over the distance, a flow rate of lymph can be calculated (Step S18).

As described above, according to this embodiment, the fluorescent dye injected into the lymph vessel is repeatedly detected and an image thereof is displayed in each case, and the pressure of the manchette 11 is repeatedly measured and output until the pressure of the manchette 11 decreases from the pressure to block the lymph flow to the pressure to restart the lymph flow. Thus, the pressure of the manchette 11 at the restart of the lymph flow can be easily recognized as lymphatic pressure. The fluorescent dye does not emit radiation, and can be obtained at low cost. Thus, according to this embodiment, lymphatic pressure can be measured with more safety and ease at lower cost without risk of exposure to radiation.

Since the manchette 11 includes the transparent portion 11b in this embodiment, the infrared camera 21 takes the image of the fluorescence so that the transparent portion 11b is included in an image taking range, and thus movement of the fluorescent dye in the lymph vessel can be detected more quickly as compared to a case where the manchette is formed of only an opaque member. Thus, timing of the restart of the lymph flow by a reduction in pressure of the manchette can be determined more quickly.

In this embodiment, the scale 11c on the transparent portion 11b can be used to measure time for the lymph flow to flow over the predetermined distance to calculate a flow rate of lymph based on the measurement.

Also, as in this embodiment, the lymphatic pressure-measuring device 10 and the lymph flow display device 20 are portable, and thus the lymphatic pressure-measuring system 1 can be used anywhere. Each of the devices can be easily handled without need for special training.

To check accuracy of the lymphatic pressure measured by this embodiment, this embodiment was compared to a method using radio isotopes and a gamma camera shown in Non-patent Literature 1 mentioned above. Specifically, for lower extremities (18 extremities) of nine subjects, measurement of the lymphatic pressure by this embodiment and measurement using scintillation counting shown in Non-patent Literature 1 mentioned above were performed, and both measurements were compared.

In this comparison, a manchette including no transparent portion was used. Pressure of the manchette was reduced in increments of 10 mmHg every five minutes in view of a flow rate of lymph, and pressure of the manchette at that time when the radio isotopes or fluorescent dye moved beyond the manchette toward a central side was determined as lymphatic pressure. If a manchette including a transparent portion is used, restart of a lymph flow can be detected and displayed in an area covered with the manchette. For example, the restart of the lymph flow can be detected more quickly and sharply while the pressure of the manchette is more finely reduced (for example, in increments of 1 mmHg).

Figure 7:
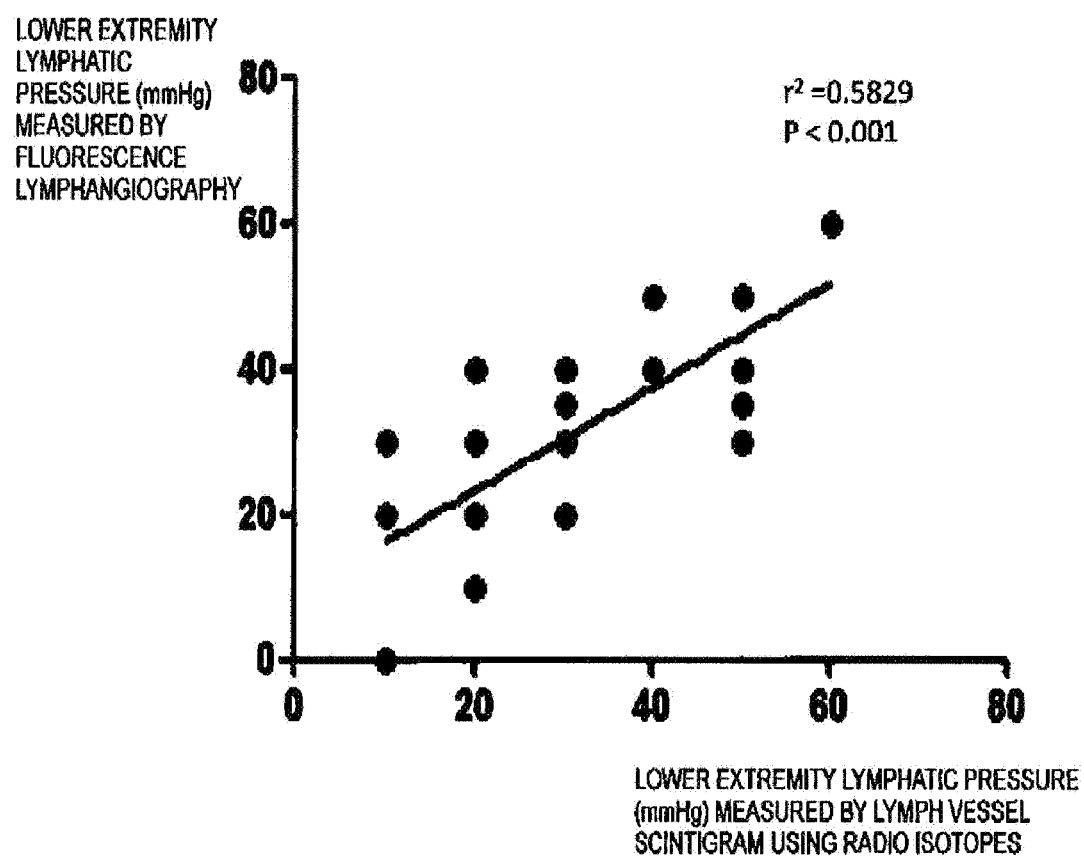
FIG. 7 is a graph showing a correlation between a method according to the first embodiment and a method using conventional scintillation counting.

A relationship between the methods is shown in a graph in FIG. 7. The ordinate in the graph represents lower extremity lymphatic pressure (mmHg) measured by this embodiment (fluorescence lymphangiography), and the abscissa represents lower extremity lymphatic pressure (mmHg) measured by lymph vessel scintigram (lymphoscintigraphy) using radio isotopes. As shown in this graph, a statistically significant correlation was obtained between values obtained by the methods (correlation coefficient $r^2=0.5829$, risk p=less than 0.001), and the accuracy of the measurement of the lymphatic pressure by the present invention was checked.

Figure 8:
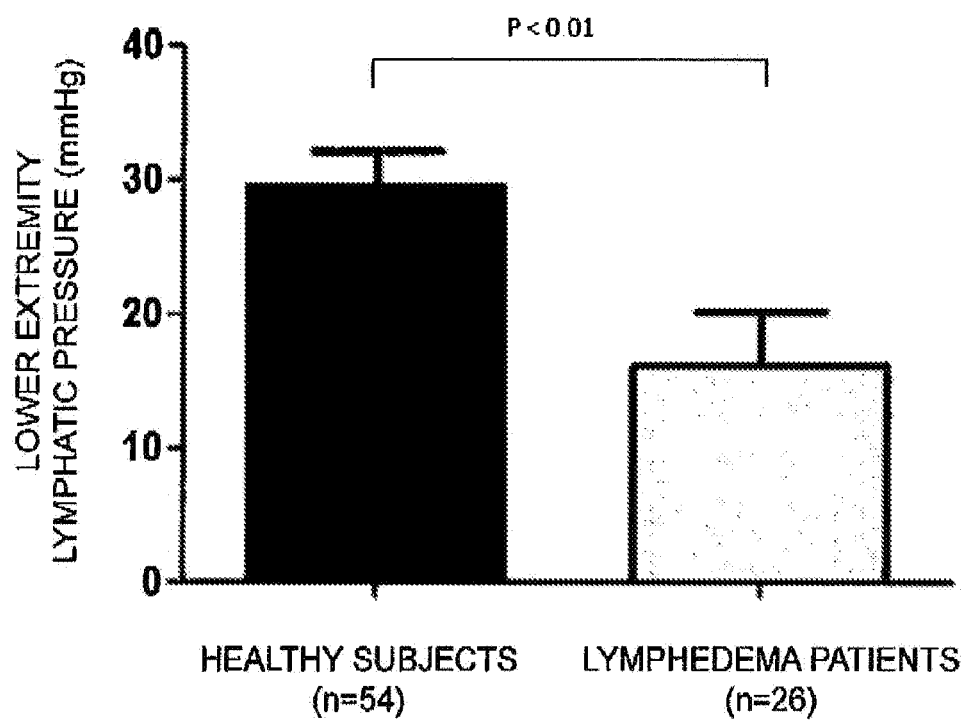
FIG. 8 is a graph showing lower extremity lymphatic pressure of healthy subjects and lymphedema patients measured by the system according to the first embodiment.

Then, the method of this embodiment was used to compare lymphatic pressure of lower extremity lymphedema patients (22 patients, 26 extremities, average age of 53) with abnormal return of lymph to that of healthy subjects (27 subjects, 54 extremities, average age of 46). As shown in a graph in FIG. 8, the lymphatic pressure of the lower extremities of the healthy subjects was 30.0±12.2 mmHg (Mean±SD), while the lymphatic pressure of the lower extremities of the lymphedema patients was 16.2±20.4 mmHg (Mean±SD) and statistically significantly lower (risk p=less than 0.01). This revealed that the level of abnormal return of lymph of lower extremities can be indicated by specific numerical values by the present invention.

As such, the lymphatic pressure-measuring system according to the present invention allows the lymphatic pressure to be measured with safety and ease at low cost, and is expected to contribute to diagnosis of lymphedema patients or insufficient return of lymph.

Figure 9:
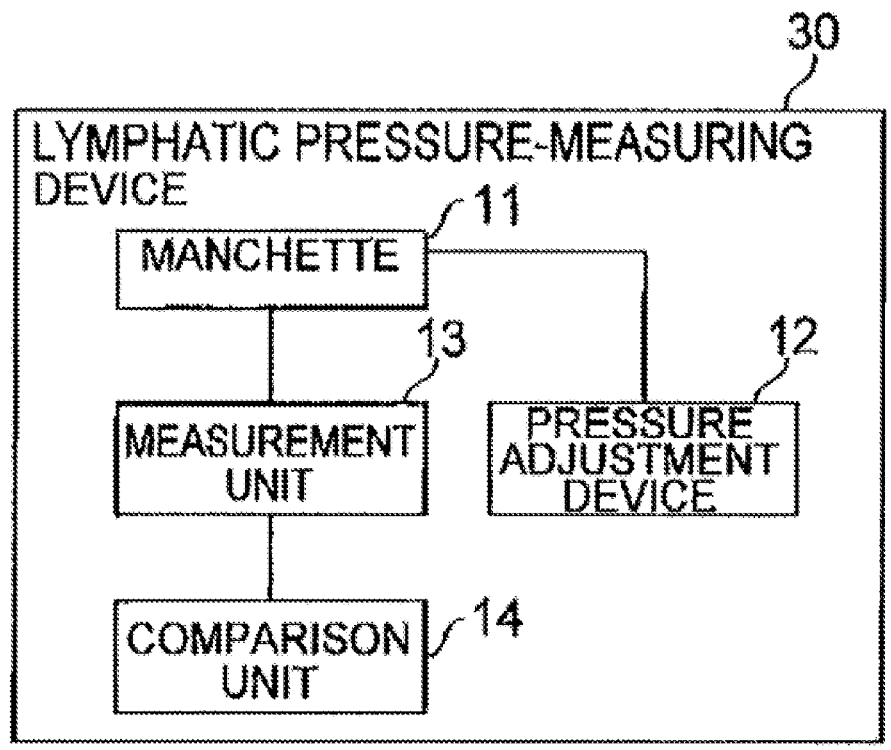
FIG. 9 is a block diagram showing a configuration of a lymphatic pressure-measuring device according to a variant of the first embodiment.

When a lymphatic pressure-measuring device is configured by application of a digital automated sphygmomanometer, the lymphatic pressure-measuring device may have a function of comparing measured lymphatic pressure to a predetermined threshold. For example, as shown in FIG. 9, a lymphatic pressure-measuring device 30 may include the manchette 11, the pressure adjustment device 12, the measurement unit 13, and also a comparison unit 14. In this case, the measurement unit 13 outputs measurement data indicating measured lymphatic pressure to the comparison unit 14. The comparison unit 14 compares the input measurement data to the threshold previously stored in a predetermined memory. The threshold is a value previously determined based on a predetermined examination and statistics, and indicating, for example, a boundary between healthy subjects and lymphedema patients or a range of lymphatic pressure at a certain age or age group.

For example, the comparison unit 14 determines whether a measured value is less than the threshold to output possibility of lymphedema, or determines whether the measured value is within a predetermined range to output a physical age based on lymphatic pressure. Thus, a user of the lymphatic pressure-measuring system can obtain information on diagnosis of lymphedema, evaluation of lymphatic aging, or the level of insufficient return of lymph.

In this embodiment, the manchette 11 includes the transparent portion 11b, and the scale 11c is formed on the transparent portion 11b, but the scale may be omitted or a manchette including no transparent portion (for example, conventional manchette) may be used. When the manchette including no transparent portion is used, the detection means such as the infrared camera need to detect fluorescence near an area around which the manchette is wrapped.

In this embodiment, the infrared camera 21 detects the fluorescence, but other devices such as a fluorescence sensor may be used as detection means. Also, predetermined image processing or information processing techniques may be used to automatically determine timing of restart of a lymph flow, and output a result thereof.

In this embodiment, the lymph flow display device 20 and the lymphatic pressure-measuring device 10 are independently configured, but these devices may communicate data with each other, or one device may have functions of the two devices. In this case, pressure of the manchette 11 at the time of automatic determination of restart of a lymph flow may be automatically measured to automatically determine and output lymphatic pressure of a subject. Thus, a user can more easily measure the lymphatic pressure.

As such, the configuration of the detection means, the configuration of the entire device, the measurement method, or the like are not limited to those shown in the first embodiment. A lymphatic pressure-measuring system 2 according to a second embodiment of the present invention will be now described.

Second Embodiment

Figure 10:
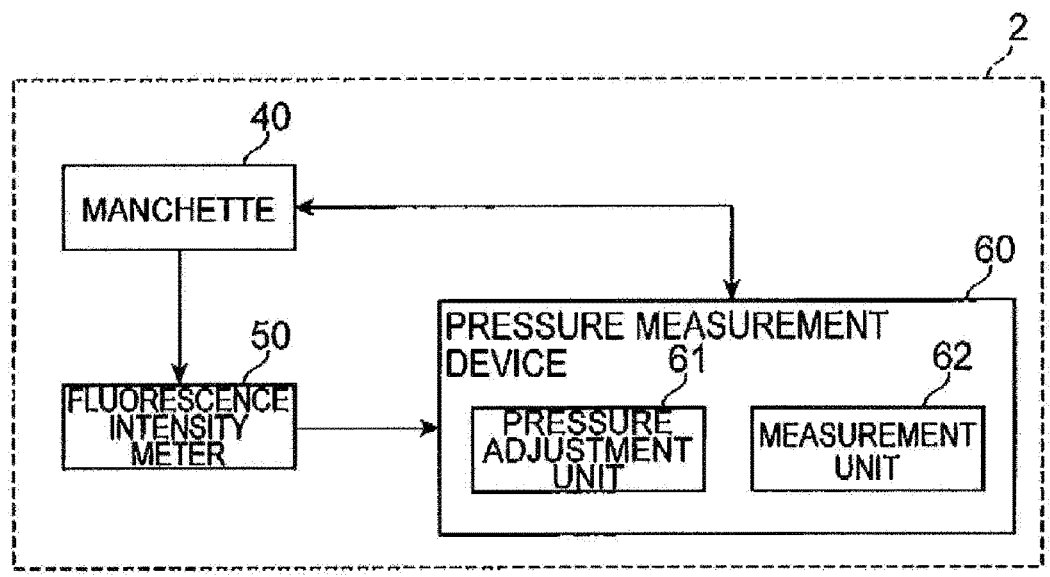
FIG. 10 is a block diagram showing a general configuration of a lymphatic pressure-measuring system according to a second embodiment.

First, with reference to FIGS. 10 and 11, a function and a configuration of a lymphatic pressure-measuring system 2 will be described. As shown in FIG. 10, the lymphatic pressure-measuring system 2 includes a manchette 40, a fluorescence intensity meter 50, and a pressure measurement device 60 as functional components.

The manchette 40 is fitted around a part of a human's arm or leg so as to cover the part like the manchette 11 in the above embodiment. The manchette 40 includes an air bag (not shown), and the pressure measurement device 60 supplies air into the air bag to pressurize the covered area (vital observation portion). As shown in FIG. 11, the manchette 40 has a band-like shape, and is secured to the arm or leg by a pair of hook and loop fasteners 41 provided at opposite edges extending along an insertion direction of the arm or leg (arrow A in the drawings).

Figure 11:
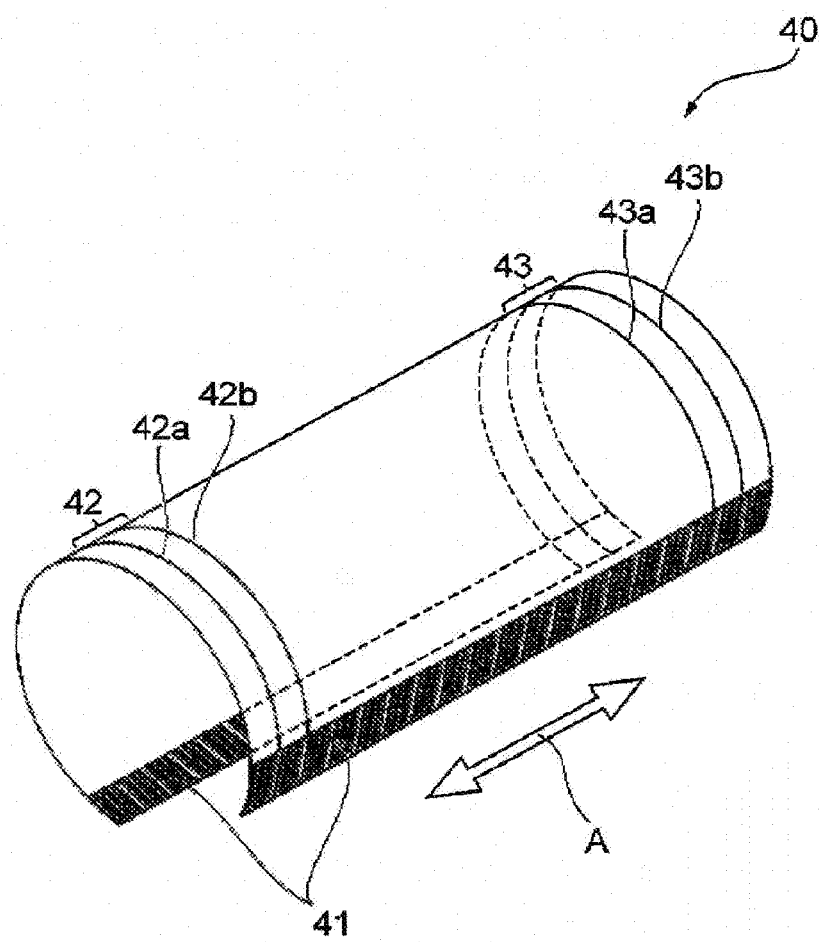
FIG. 11 is a schematic diagram showing an example of a manchette in FIG. 10.

As shown in FIG. 11, the manchette 40 includes a first detection unit 42 and a second detection unit 43. In this specification, for convenience, when the manchette 40 is fitted on the vital observation portion, a detection unit (detection unit on a peripheral side) closer to an injection point of fluorescent dye is a first detection unit 42, and a detection unit (detection unit on a central side) remoter from the injection point is a second detection unit 43. The first detection unit 42 includes a first line LED 42a and a first line sensor 42b, and the second detection unit 43 includes a second line LED 43a and a second line sensor 43b. The line LEDs 42a and 43a are illumination means that apply an excitation light to fluorescent dye injected into a lymph vessel, and light up in measurement. Meanwhile, the line sensors 42b and 43b are light receiving means that detect fluorescence emitted from the fluorescent dye having received the excitation light, and output signals indicating intensity of the detected fluorescence to the fluorescence intensity meter 50.

The first line LED 42a and the first line sensor 42b are linearly (continuously) provided over one edge extending in a width direction of the manchette 40 so as to be adjacent to each other. The second line LED 43a and the second line sensor 43b are linearly (continuously) provided over the other edge extending in the width direction of the manchette 40 so as to be adjacent to each other. Thus, when the manchette 40 is wrapped around the arm or leg, the first detection unit 42 and the second detection unit 43 surround the arm or leg. The width direction of the manchette 40 is a direction perpendicular to the insertion direction of the arm or leg.

A wavelength of excitation light emitted from the line LEDs 42a and 43a is different from a wavelength of fluorescence emitted from the fluorescent dye having received the excitation light and detected by the line sensors 42b and 43b. For example, when a wavelength of excitation light applied to indocyanine green is 805 nm, a wavelength of fluorescence from the indocyanine green is 845 nm. It is natural that the wavelength of the excitation light emitted from the line LEDs 42a and 43a and the wavelength of the fluorescence detected by the line sensors 42b and 43b are not limited to the above, but may be set depending on types of fluorescent dye.

The fluorescence intensity meter 50 is electrically connected to the two line sensors 42b and 43b of the manchette 40, displays intensity of fluorescence at the two edges extending in the width direction of the manchette 40 based on signals input from the line sensors 42b and 43b. Thus, a user of the lymphatic pressure-measuring system 2 can visually recognize whether the fluorescent dye has passed through two areas surrounded by the line sensors 42b and 43b.

The fluorescence intensity meter 50 determines whether the fluorescent dye has passed through the two areas surrounded by the line sensors 42b and 43b based on input signals, and outputs passage signals that indicate first passage of the fluorescent dye through the two areas to the pressure measurement device 60. Thus, in one measurement, two passage signals are output from the fluorescence intensity meter 50. The first passage signal means that the fluorescent dye has passed below the first line sensor 42b closer to the injection point of the fluorescent dye (on the peripheral side). In contrast to this, the second passage signal means that the fluorescent dye has passed through the area covered with the manchette 40, and passed below the second line sensor 43b remoter from the injection point (on the central side of the body).

The fluorescence intensity meter 50 may determine passage of the fluorescent dye based on magnitude of changes of fluorescence intensity, and determine that the fluorescent dye has passed when the detected intensity reaches a threshold or more previously stored therein. Of course, a specific determination method is not limited thereto.

The pressure measurement device 60 measures pressure of the manchette 40. The pressure measurement device 60 is connected to the manchette 40 via a pipe for supplying or sucking air to or from the manchette 40, and electrically connected to the fluorescence intensity meter 50. The pressure measurement device 60 includes a pressure adjustment unit 61 and a measurement unit 62 as functional components.

As the pressure measurement device 60, a lymphatic pressure meter or a sphygmomanometer may be used. A measurement device that can both measure lymphatic pressure and blood pressure may be used as the pressure measurement device 60.

The pressure adjustment unit 61 adjusts pressure of the manchette 40. The pressure adjustment unit 61 starts supplying air into the air bag in the manchette 40 when the first passage signal is input from the fluorescence intensity meter 50, and pressurizes the manchette 40 so as to block a lymph flow in the vital observation portion (for example, at 60 mmHg). Then, the pressure adjustment unit 61 reduces pressure of the manchette 40 at predetermined timing in increments of a predetermined amount (for example, in increments of 1 mmHg, 5 mmHg, or 10 mmHg) until the second passage signal is input.

The measurement unit 62 measures the pressure of the manchette 40. The measurement unit 62 starts pressure measurement and clocking when the first passage signal is input from the fluorescence intensity meter 50. Then, when the second passage signal is input, the measurement unit 62 records the pressure of the manchette 40 at that time as lymphatic pressure, and outputs the value of the lymphatic pressure via a monitor or the like. The measurement unit 62 calculates a flow rate of lymph based on time between the start of clocking and the input of the second passage signal, and a distance between the two line sensors 42b and 43b, and outputs a calculation result via the monitor or the like. Thus, the user of the lymphatic pressure-measuring system 2 can recognize the lymphatic pressure or the flow rate of lymph of the subject.

Figure 12:
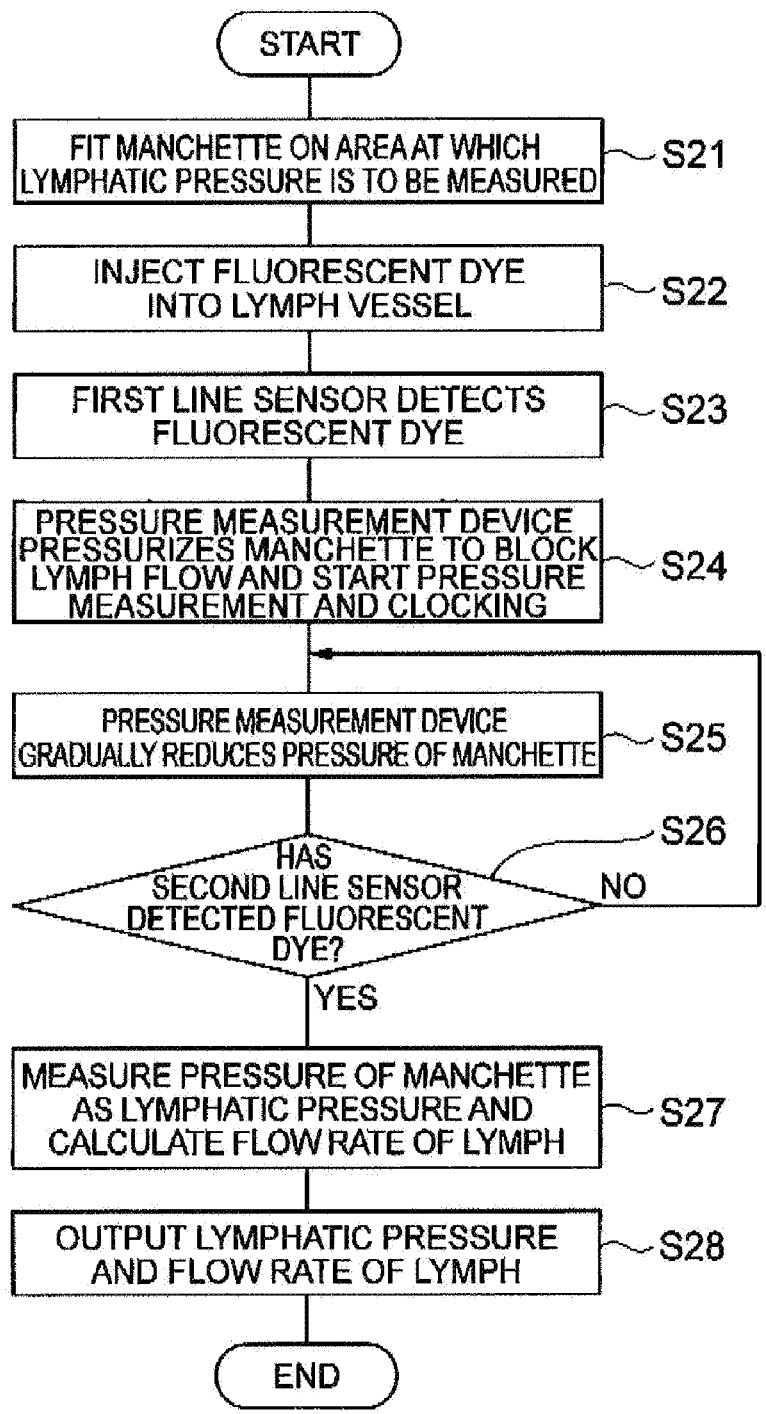
FIG. 12 is a flowchart showing a process by the lymphatic pressure-measuring system in FIG. 10.

Next, with reference to FIGS. 12 and 13, a procedure for measuring the lymphatic pressure of the subject's extremity using the lymphatic pressure-measuring system 2 will be described, and an operation of the lymphatic pressure-measuring system 2 will be described.

First, the manchette 40 is fitted on an area at which lymphatic pressure is to be measured (vital observation portion), and the two line LEDs 42a and 43a are lit to detect fluorescent dye (Step S21). Fluorescent dye (for example, indocyanine green) is intradermically or subcutaneously injected, reaching lymph vessel of a subject (Step S22). These processes are basically the same as the processes in Steps S11 and S12 in FIG. 5.

FIG. 13A shows fluorescent dye F immediately after injected intradermically or subcutaneously into the back of a foot. Then, the fluorescent dye F starts to move from the injection point through a lymph vessel toward center of the body as show in FIG. 13B. Then, as shown in FIG. 13C, when the fluorescent dye F reaches one end (the edge closer to the injection point of the fluorescent dye) of the manchette 40, the fluorescent dye F receives excitation light from the first line LED 42a to emit fluorescence, and the first line sensor 42b detects the fluorescence (Step S23).

According to the detection, the fluorescence intensity meter 50 determines that the fluorescent dye has passed below the first line sensor 42b. By this determination, the pressure adjustment unit 61 in the pressure measurement device 60 pressurizes the manchette 40 to block the lymph flow in the vital observation portion (Step S24). Thus, the state shown in FIG. 13 C is maintained. At this time, the measurement unit 62 starts pressure measurement and clocking (Step S24).

Then, the pressure adjustment unit 61 gradually reduces the pressure of the manchette 40, and the measurement unit 62 continues pressure measurement and clocking (Step S25). Then, if intrinsic (autonomous) contractility of the lymph vessel exceeds the pressure of the manchette 40 by the pressure reduction, the fluorescent dye F starts to move toward the center (restart of the lymph flow), and at least a part of the fluorescent dye F reaches the other end (the edge remoter from the injection point of the fluorescent dye) of the manchette 40 as shown in FIG. 13D. At this time, the fluorescent dye F having reached the other end receives the excitation light from the second line LED 43a to emit fluorescence, and the second line sensor 43b detects the fluorescence (Step S26; YES).

According to the detection, the fluorescence intensity meter 50 determines that the fluorescent dye has passed below the second line sensor 43b. Then, by this determination, the measurement unit 62 in the pressure measurement device 60 measures the pressure of the manchette 40 at that time as lymphatic pressure, and calculates a flow rate of lymph (Step S27). Then, the measurement unit 62 outputs the measured lymphatic pressure and the calculated flow rate of lymph via a monitor or the like (Step S28). Thus, measurement of the lymphatic pressure is finished. The fluorescent dye F then further advances toward the center of the body as shown in FIG. 13E.

As described above, according to this embodiment, when the fluorescent dye injected into the lymph vessel is detected at one point (first detection unit 42) in the manchette 40, the manchette 40 is pressurized to block the lymph flow in the vital observation portion. Then, the pressure of the manchette 40 is gradually reduced to restart the lymph flow, and when the fluorescent dye on the lymph flow is detected at a different point (second detection unit 43) in the manchette 40, the pressure of the manchette 40 at that time is measured. As such, movement of the fluorescent dye is detected to automatically adjust and measure the pressure of the manchette 40, and thus the pressure of the manchette 40 at the restart of the lymph flow can be easily recognized as lymphatic pressure. Thus, the lymphatic pressure can be measured with more safety and ease at lower cost without risk of exposure to radiation. Also in this embodiment, the same advantage as in the first embodiment can be obtained.

In this embodiment, the excitation light is applied to the fluorescent dye, and thus the fluorescent dye that emits fluorescence only when a light having a specific wavelength is applied can be used, and fluorescent dye having various wavelength characteristics (having specific excitation light wavelengths) can be used. Thus, only the wavelength of the fluorescence emitted from the fluorescent dye can be detected, and light having other wavelengths can be filtered, and thus the lymph flow can be detected more accurately (with higher sensitivity) and specifically.

In this embodiment, the two detection units 42 and 43 may be provided at the opposite edges of the manchette 40, and thus the manchette 40 can be easily produced. The two detection units 42 and 43 are linearly provided at the opposite edges of the manchette 40. Thus, a fluorescence trapping range when the manchette 40 is fitted on the vital observation portion can be broadened to more reliably detect fluorescence.

In this embodiment, the fluorescence intensity meter 50 displays fluorescence intensity, but this display function may be omitted.

In this embodiment, the two detection units 42 and 43 are provided at the edges extending in the width direction of the manchette 40. However, the positions of the first and second detection means are not limited thereto, but for example, the detection means may be provided inside the edges. Also, in this embodiment, the detection units 42 and 43 are linearly (continuously) provided, but the detection means may be provided at predetermined intervals (discontinuously) in the width direction of the manchette 40. In this embodiment, the detection units 42 and 43 include the line LEDs 42a and 43a, respectively, but such illumination means may be omitted.

In this embodiment, the manchette 40 includes the two detection units 42 and 43, but more detection units may be provided in the manchette. For example, the detection units are provided at the opposite edges extending along the width direction of the manchette as shown in FIG. 11, and one or more further detection units may be provided between the two detection units. Three or more detection units are thus provided at predetermined intervals in the insertion direction of the arm or leg, thereby allowing advance of lymph from the peripheral side to the central side to be observed in more detail.

The present invention has been described above in detail based on the embodiments. However, the present invention is not limited to the embodiments. The present invention may be changed in various manners without departing from the gist thereof.

REFERENCE SIGNS LIST

1 . . . lymphatic pressure-measuring system, 10, 30 . . . lymphatic pressure-measuring device, 11 . . . manchette, 11b . . . transparent portion, 11c . . . scale, 12 . . . pressure adjustment device, 13 . . . measurement unit (measurement means), 14 . . . comparison unit, 20 . . . lymph flow display device, 21 . . . infrared camera (detection means), 22 . . . image processing device (display means), 23 . . . processing unit, 24 . . . display unit, 25 . . . storage unit, 2 . . . lymphatic pressure-measuring system, 40 . . . manchette, 42 . . . first detection unit (first detection means), 42a . . . first line LED (light application means), 42b . . . first line sensor (light receiving means), 43 . . . second detection unit (second detection means), 43a . . . second line LED (light application means), 43b . . . second line sensor (light receiving means), 50 . . . fluorescence intensity meter, 60 . . . pressure measurement device, 61 . . . pressure adjustment unit (pressure adjustment means), 62 . . . measurement unit (measurement means)

The invention claimed is:

1. A method for determining a lymphatic parameter, comprising:
    fitting a manchette on an observation portion of a subject, at least a part of the manchette comprising an elongated transparent member extending along a direction of lymph flow in the subject, wherein a scale is formed on the transparent member;
    injecting a fluorescent dye into the subject;
    pressurizing the manchette;
    reducing a pressure of the manchette;
    detecting a fluorescence emitted from the fluorescent dye in a lymph vessel of the subject via the transparent member by an infrared camera so that the transparent member is included within an image taking range of the infrared camera and outputting a detected signal; and
    determining the lymphatic parameter based on the detected signal, wherein the detecting step is performed when the pressure of the manchette is reduced.

2. The method according to claim 1, wherein the fluorescent dye is indocyanine green.

3. The method according to claim 1, wherein the lymphatic parameter is at least one of a lymphatic pressure, a flow rate of lymph, information on diagnosis of lymphedema, information on evaluation of lymphatic aging, and information on a level of insufficient return of lymph.

4. The method according to claim 1, wherein the detecting includes measuring the pressure of the manchette when a lymph flow restarts.

5. A method for detecting a lymphatic parameter, comprising:
    fitting a band comprising a plurality of light sources and a plurality of light detectors on an observation portion of a subject so that the plurality of light sources and the plurality of light detectors surround the observation portion, the band further comprising a transparent member wherein a scale is formed on the transparent member;
    injecting a fluorescent dye into the subject;
    irradiating the observation portion with an excitation light by the plurality of light sources;
    detecting a fluorescence emitting from the fluorescent dye in a lymph vessel of the subject by the plurality of light detectors, and outputting a detected signal; and
    determining the lymphatic parameter based on the detected signal, wherein the plurality of light sources and the plurality of light detectors are provided in a first direction of the band so as to be adjacent to each other.

6. The method of claim 5 wherein the band comprises a manchette.

7. The method of claim 6 wherein the manchette comprises a) a first light detector and first light source at a first edge of the manchette, and b) a second light detector and second light source at an opposite second edge of the manchette.

* * * * *